United States Patent
Ebinuma et al.

(10) Patent No.: US 11,155,805 B2
(45) Date of Patent: Oct. 26, 2021

(54) TARGET NUCLEIC ACID CONCENTRATION AND RECOVERY METHOD USING ANTIBODY

(71) Applicant: SEKISUI MEDICAL CO., LTD., Tokyo (JP)

(72) Inventors: Hiroyuki Ebinuma, Tokyo (JP); Katsura Uchida, Tokyo (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 124 days.

(21) Appl. No.: 16/482,164

(22) PCT Filed: Mar. 27, 2018

(86) PCT No.: PCT/JP2018/012354
§ 371 (c)(1),
(2) Date: Jul. 30, 2019

(87) PCT Pub. No.: WO2018/181274
PCT Pub. Date: Oct. 4, 2018

(65) Prior Publication Data
US 2019/0376057 A1 Dec. 12, 2019

(30) Foreign Application Priority Data
Mar. 27, 2017 (JP) .............................. JP2017-060842

(51) Int. Cl.
| C12N 15/10 | (2006.01) |
| C07H 1/06 | (2006.01) |
| C07H 21/04 | (2006.01) |
| C07K 1/36 | (2006.01) |

(52) U.S. Cl.
CPC ........... *C12N 15/1006* (2013.01); *C07H 1/06* (2013.01); *C07H 21/04* (2013.01); *C07K 1/36* (2013.01)

(58) Field of Classification Search
CPC ...... C12N 15/1006; C07H 1/06; C07H 21/04; C07K 1/36
USPC ...................................................... 536/25.4
See application file for complete search history.

(56) References Cited

U.S. PATENT DOCUMENTS
| 2002/0004211 A1 | 1/2002 | Keene et al. |
| 2005/0069931 A1 | 3/2005 | Allis et al. |
| 2010/0240054 A1 | 9/2010 | Bischoff |

FOREIGN PATENT DOCUMENTS
| JP | 2004-520002 A | 7/2004 |
| JP | 2005-517431 A | 6/2005 |
| JP | 2010-539906 A | 12/2010 |
| WO | WO 2009/039507 A2 | 3/2009 |
| WO | WO 2016/156353 A1 | 10/2016 |
| WO | WO 2016/187234 A1 | 11/2016 |

OTHER PUBLICATIONS

Dhumpa et al. Rapid detection of avian influenza virus in chicken fecal samples by immunomagnetic capture reverse transcriptase-polymerase chain reaction assay. Diagnostic Microbiology and Infectious Disease 69 (2011) 258-265. (Year: 2011).*
Geng et al. Histone modification analysis by chromatin immunoprecipitation from a low number of cells on a microfluidic platform. Lab Chip, 2011, 11, 2842. (Year: 2011).*
International Preliminary Report on Patentability and Written Opinion of the International Searching Authority for International Application No. PCT/JP2018/012354, dated Oct. 3, 2019, with an English translation.
Boom et al., "Rapid and Simple Method for Purification of Nucleic Acids," Journal of Clinical Microbiology, vol. 28, No. 3, Mar. 1990, pp. 495-503.
English translation of the International Search Report dated Jun. 26, 2018, for International Application No. PCT/JP2018/012354.
Japanese Office Action, dated Jul. 17, 2019, for Japanese Application No. 2019-509867, with an English translation.
Kahramanoglou et al., "Direct and Indirect Effects of H-NS and Fis on Global Gene Expression Control in *Escherichia coli*," Nucleic Acids Research, vol. 39, No. 6, 2011 (Published online Nov. 21, 2010, pp. 2073-2091.

(Continued)

*Primary Examiner* — Yih-Horng Shiao
(74) *Attorney, Agent, or Firm* — Birch, Stewart, Kolasch & Birch, LLP

(57) ABSTRACT

An object of the present invention is to provide an efficient nucleic acid recovery method capable of concentrating a nucleic acid from a sample containing a nucleic acid such that the nucleic acid is usable in gene amplification reaction. To solve the problem, the present inventors have found that by targeting a protein to which a nucleic acid is bound (hereinafter also referred to as a nucleoprotein or a protein-nucleic acid complex) rather than targeting the nucleic acid itself, or specifically, by causing a specific antibody against the protein to act, the nucleic acid can be captured simultaneously with the protein, and thereby completing the present invention. Furthermore, the present inventors have found that if animal cells, bacteria, viruses, etc. have a nucleic acid bound to protein present in a cell (in an envelope in the case of viruses), the bound nucleic acid can be captured and recovered by using a specific antibody against the nucleoprotein without dissociating the nucleic acid from the protein after treating the cell with a surfactant.

21 Claims, 3 Drawing Sheets
Specification includes a Sequence Listing.

(56) References Cited

OTHER PUBLICATIONS

Rekha et al., "Pullulan-histone Antibody Nanoconjugates for the Removal of Chromatin Fragments from Systemic Circulation," Biomaterials, vol. 34, 2013, (Available online Jun. 5, 2013), pp. 6328-6338.

Snyder et al., "Cell-free DNA Comprises an In Vivo Nucleosome Footprint that Informs Its Tissues-of-Origin," Cell, vol. 164, Jan. 14, 2016, pp. 57-68 (13 total pages).

Yamashita, "Chromatin Immunoprecipitation (ChIP Assay)," Surgery Frontier, vol. 13, No. 2, 2006, pp. 96-101.

* cited by examiner

[FIG.1]
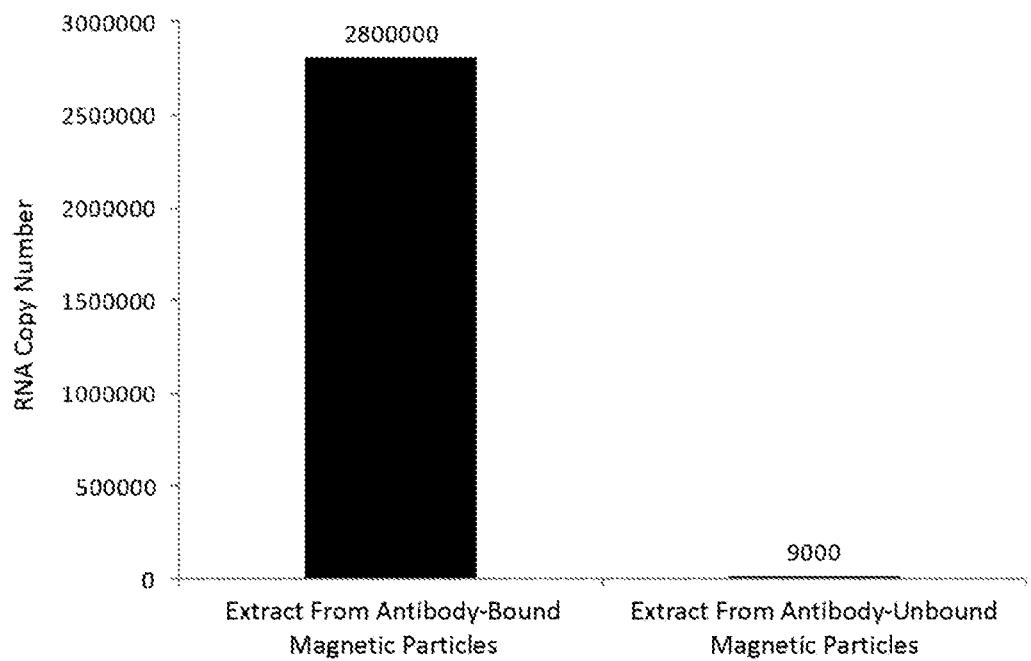
[FIG.2]
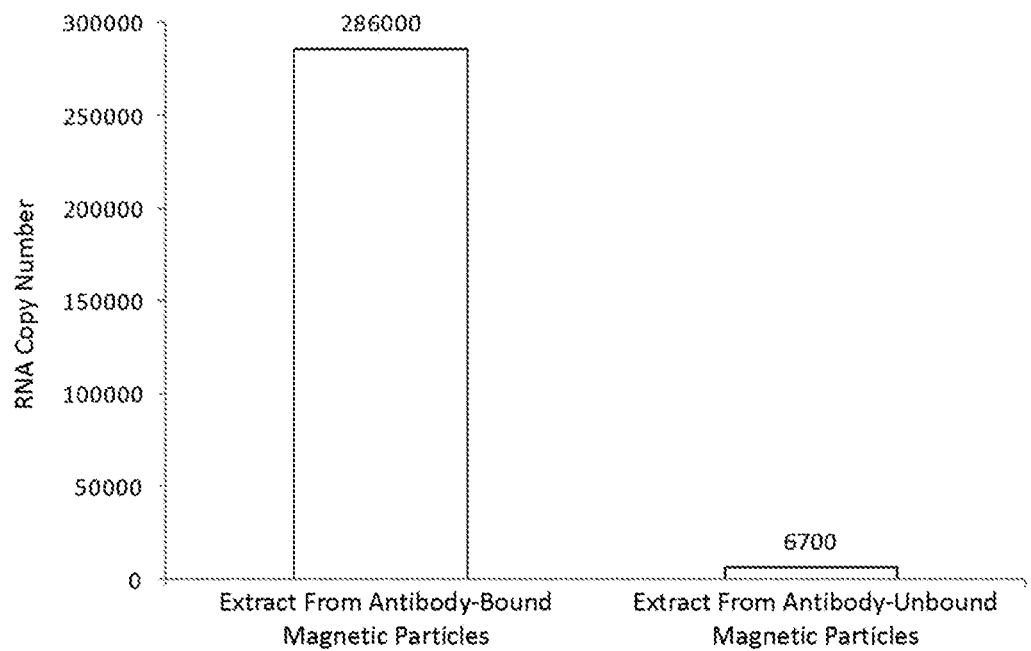

[FIG.3]
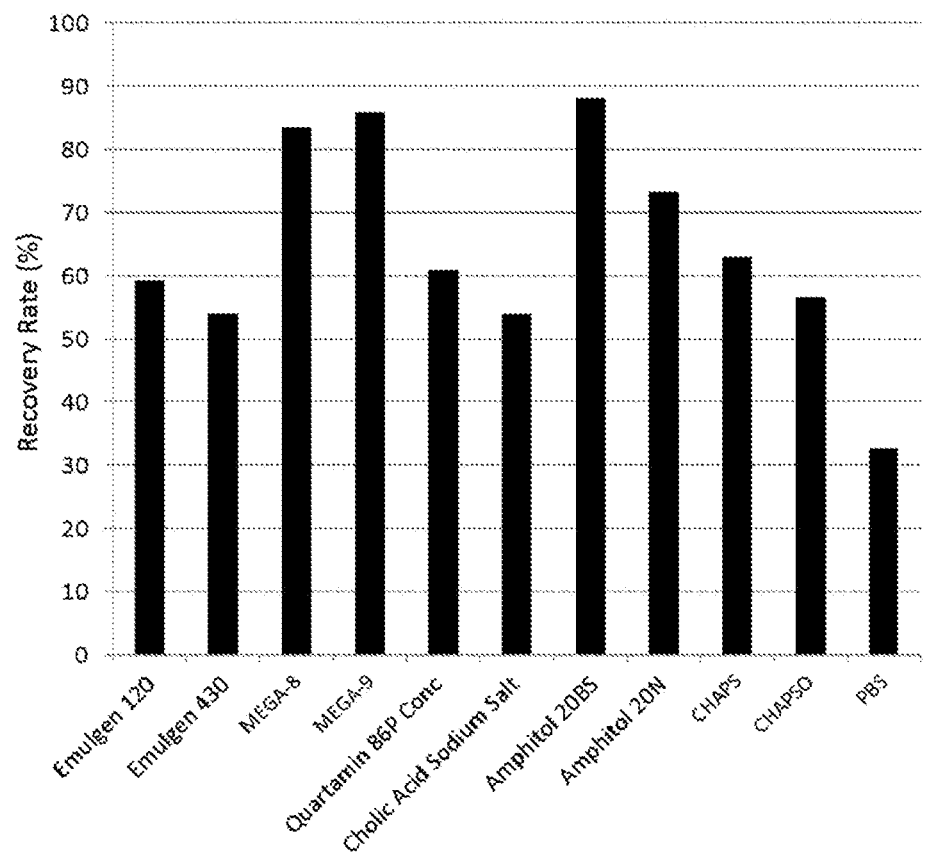

[FIG.4]
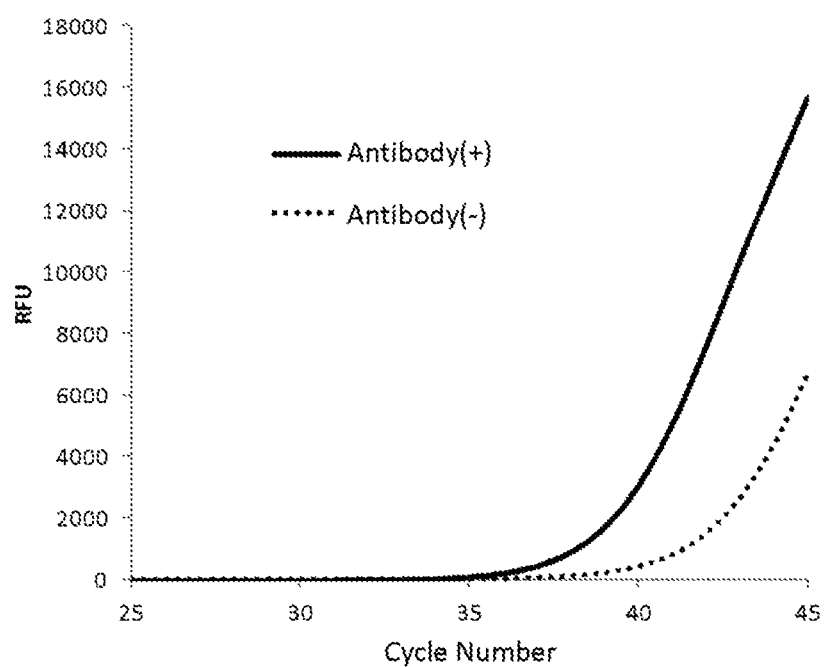

SEQUENCE LISTING

```
<160> NUMBER OF SEQ ID NOS: 8

<210> SEQ ID NO 1
<211> LENGTH: 22
<212> TYPE: DNA
<213> ORGANISM: Artificial Sequence
<220> FEATURE:
<223> OTHER INFORMATION: primer

<400> SEQUENCE: 1
cagtaccaat gaactggcga ca                                            22

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
agctggaatc aacaaggatt tacc                                          24

<210> SEQ ID NO 3
<211> LENGTH: 18
<212> TYPE: DNA
<213> ORGANISM: Artificial Sequence
<220> FEATURE:
<223> OTHER INFORMATION: TaqMan probe
<220> FEATURE:
<221> NAME/KEY: misc_feature
<222> LOCATION: (1)..(1)
<223> OTHER INFORMATION: modified with FAM
<220> FEATURE:
<221> NAME/KEY: misc_feature
<222> LOCATION: (18)..(18)
<223> OTHER INFORMATION: modified with quencher

<400> SEQUENCE: 3
tgaatagatc gccaaaat                                                 18

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
aacacaaatt gaggtgggtc                                               20

<210> SEQ ID NO 5
<211> LENGTH: 26
<212> TYPE: DNA
<213> ORGANISM: Artificial Sequence
<220> FEATURE:
<223> OTHER INFORMATION: primer
```

```
<400> SEQUENCE: 5
ctttcatagc actcyagaat tcctgc                                              26

<210> SEQ ID NO 6
<211> LENGTH: 19
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (1)..(1)
<223> OTHER INFORMATION: modified with FAM
<220> FEATURE:
<221> NAME/KEY: misc_feature
<222> LOCATION: (19)..(19)
<223> OTHER INFORMATION: modified with quencher

<400> SEQUENCE: 6
caaccaatgc caccataaa                                                      19

<210> SEQ ID NO 7
<211> LENGTH: 17
<212> TYPE: DNA
<213> ORGANISM: Artificial Sequence
<220> FEATURE:
<223> OTHER INFORMATION: primer

<400> SEQUENCE: 7
ccgtgcatct catcttg                                                        17

<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8
ctttgtgttc ccggacatag tc                                                  22
```

TARGET NUCLEIC ACID CONCENTRATION AND RECOVERY METHOD USING ANTIBODY

TECHNICAL FIELD

The present invention relates to a technique of concentrating and recovering a target nucleic acid from a sample containing a nucleic acid such as a biological sample.

BACKGROUND ART

The Boom method (Non-Patent Document 1) is widely applied as a method of concentrating and recovering a nucleic acid from a biological sample, bacteria, viruses, etc. In this method, first, a nucleic acid is bound to silica gel particles in the presence of a chaotropic salt containing thiocyanate ions, chlorate ions, etc., and the silica beads are then washed with an approximately 70% alcohol aqueous solution (such as an ethanol aqueous solution and an isopropanol aqueous solution) to remove the chaotropic salt and contaminants. Subsequently, the silica beads are dried to remove alcohol (such as ethanol and isopropanol), and the nucleic acid adsorbed to the silica beads can then be separated and recovered with a low concentration buffer or water. The recovered nucleic acid is applicable to a gene amplification reaction (PCR (Polymerase Chain Reaction), LAMP (Loop-Mediated Isothermal Amplification), etc.), a gene amplification reaction combined with reverse transcription (Reverse Transcription PCR (RT-PCR), LAMP using a reverse transcriptase, etc.).

Nucleic acids recovered from human biological samples (blood, urine, tissues, etc.) are used for disease diagnosis and as indicators for prediction of effects of therapeutic agents. For example, a mutation examination of EGFR (Epidermal Growth Factor Receptor) gene for a lung cancer patient is performed by using DNA concentrated and recovered from lung cancer tissues with the boom method etc. and has already been clinically applied as an important examination for determining the effect of treatment with a tyrosine kinase inhibitor. In general, a biopsy, i.e., collection of a piece of tissue for biopsy purposes, from a cancer patient is highly invasive. Especially for patients with lung cancer liable to recurrence, biopsies are frequently required but are difficult in many cases due to problems of invasiveness. As a substitute, a method of recovering and examining DNA fragments circulating in blood (ccfDNA; circulating cell free DNA) is also studied in recent years. Eukaryotic chromosomal DNA is known to wrap around a histone protein, and when cell death occurs due to apoptosis, DNA is broken in a region not wrapping around the histone protein; thus, it is reported that only the region wrapping around the histone protein can exist as ccfDNA without being broken (Non-Patent Document 2). This ccfDNA can also be recovered as a DNA fragment by applying the boom method, and a kit has already been sold ("QIAamp Circulating Nucleic Acid Kit", Catalog No. 55114, manufactured by Qiagen).

Bacterial and viral test for infectious disease examinations are clinically applied as POC testing such as immunochromatography using specific antibodies against cell membranes and intracellular proteins. Among them, particularly for influenza infections, POC testing often causes false negatives due to lack of sensitivity in the early stage of infection, and a high sensitivity detection system using influenza virus RNA has also been developed. The influenza virus RNA is known to wrap in a helical manner around a nucleoprotein called NP protein inside the envelope, and this RNA can be recovered by a method utilizing the boom method.

Patent Document 1 discloses a method of isolating and characterizing an endogenous mRNP complex using a ligand which binds to an RNA binding protein or an RNA-associated protein contained in a cellular mRNA protein (mRNP) complex, a binding molecule specific to the ligand, and a solid support to which the binding molecule is attached.

CITATION LIST

Patent Literature

Patent Document 1: Japanese Unexamined Patent Application Publication (Translation of PCT Application) No. 2004-520002

Non Patent Literature

Non-Patent Document 1: J. Clin. Microbiol. 1990 (28) 495-503.
Non-Patent Document 2: Cell, 2016 (164) 57-68.

SUMMARY OF INVENTION

Technical Problem

In the booming method or a method of concentrating and recovering a nucleic acid to which the boom method is applied, when the concentrated and recovered nucleic acid is used as a template for an amplification reaction, the reaction may be inhibited if chaotropic salt is mixed in, and therefore, it is required to sufficiently wash silica beads with high concentration alcohol (approximately 70% alcohol aqueous solution such as ethanol aqueous solution, isopropanol aqueous solution, etc.) without causing dissociation of the nucleic acid adsorbed thereto. Furthermore, since the reaction may be inhibited if alcohol in the washing solution is mixed in, a sufficient drying operation of the silica beads is required. Therefore, it has been desired to achieve a reduction in time and simplification of a nucleic acid recovery operation by eliminating the use of chaotropic salt and alcohol.

An object of the present invention is to provide an efficient nucleic acid recovery method capable of concentrating a nucleic acid from a sample containing a nucleic acid without using chaotropic salt or alcohol.

Solution to Problem

To solve the problem, the present inventors have found that by using a protein to which a nucleic acid is bound (hereinafter also referred to as a nucleoprotein or a protein-nucleic acid complex) as a target rather than using the nucleic acid itself as a target, or specifically, by causing a specific antibody against the protein to act, the nucleic acid can be captured simultaneously with the protein, and thereby completing the present invention. Furthermore, the present inventors have found that if animal cells, bacteria, viruses, etc. have a nucleic acid bound to protein present in a cell (in an envelope in the case of viruses), a nucleic acid bound to a nucleoprotein can be treated with a surfactant and thereby captured, concentrated, and recovered by using a specific antibody against the nucleoprotein without dissociating the nucleic acid from the protein for concentration and recovery (the term "concentrate/concentrating/concentrated/concentration" may be paraphrased as "extract/extracting/extracted/extraction" or "capture/capturing/captured", the same applies hereinafter).

Therefore, the present invention provides the following [Embodiment 1] to [Embodiment 27].

Embodiment 1

A method of concentrating a nucleic acid, comprising the following steps (a) to (c):
(a) providing a sample containing a protein-nucleic acid complex in which a protein and a nucleic acid are bound:
(b) bringing the sample, an antibody specifically reactive with the protein, and a carrier which can adsorb the antibody into contact with each other; and
(c) recovering the carrier from the sample to obtain a concentrated nucleic acid on the carrier.

Embodiment 2

The method according to Embodiment 1, further comprising a step of (d) separating the concentrated nucleic acid from the carrier.

Embodiment 3

The method according to Embodiment 1 or 2, wherein at step (b), the carrier brought into contact is an antibody-supporting carrier in which the antibody is supported by the carrier.

Embodiment 4

The method according to Embodiment 3, wherein at step (d), the nucleic acid is released from the protein-nucleic acid complex attached to the antibody-supporting carrier by an immunoreaction.

Embodiment 5

The method according to any one of Embodiments 1 to 4, wherein at step (b), the antibody and the protein-nucleic acid complex are bound to each other to form an antibody-protein-nucleic acid complex.

Embodiment 6

The method according to Embodiment 5, wherein at step (d), the nucleic acid is released from the antibody-protein-nucleic acid complex adsorbed to the carrier by physical adsorption.

Embodiment 7

The method according to Embodiments 1 to 6,
further comprising the following step (a') before step (a), at step (a), or between step (a) and step (b):
(a') adding a surfactant to a sample containing the protein-nucleic acid complex.

Embodiment 8

The method according to Embodiment 7, wherein the surfactant is one or more selected from nonionic surfactants, cationic surfactants, anionic surfactants, and amphoteric surfactants.

Embodiment 9

The method according to any one of Embodiments 1 to 8, wherein the sample is one or more selected from a biological sample and a sample containing a pathogenic microorganism or virus.

Embodiment 10

The method according to Embodiment 9, wherein the biological sample is an animal cell.

Embodiment 11

The method according to Embodiment 10, wherein the biological sample is one or more selected from blood, plasma, serum, urine, feces, bile, pancreatic juice, nasal discharge, and nasal cavity/pharyngeal swab.

Embodiment 12

The method according to Embodiment 9, wherein the sample containing a pathogenic microorganism or virus is a culture of a pathogenic microorganism or virus.

Embodiment 13

The method according to Embodiment 9, wherein the virus is an influenza virus.

Embodiment 14

The method according to any one of Embodiments 1 to 13, wherein the protein is a nucleoprotein.

Embodiment 15

The method according to Embodiment 14, wherein the nucleoprotein is one or more selected from histone and nucleocapsid protein.

Embodiment 16

The method according to any one of Embodiments 1 to 15, wherein the antibody specifically reactive with the protein-nucleic acid complex is an antibody recognizing a nucleoprotein.

Embodiment 17

The method according to Embodiment 16, wherein the antibody recognizing a nucleoprotein is one or more selected from an anti-histone antibody and an antibody recognizing a nucleocapsid protein.

Embodiment 18

The method according to any one of Embodiments 1 to 17, wherein the nucleic acid is a nucleic acid excluding messenger RNA (mRNA).

Embodiment 19

The method according to any one of Embodiments 1 to 18, wherein the nucleic acid is selected from the group consisting of algal DNA, algal RNA, archaeal DNA, archaeal RNA, bacterial DNA, bacterial RNA, catalytic DNA, circular DNA, concatenated DNA, cruciform DNA, fungal DNA, fungal RNA, helminth DNA, helminth RNA, intergenic DNA, isochore, microRNA, neoplasm DNA, neoplasm RNA, nuclear RNA, plant DNA, plant RNA, protozoan DNA, protozoan RNA, recombinant DNA, retroelement, ribosomal DNA, ribosomal RNA, satellite DNA, satellite RNA, transfer RNA, untranslated RNA, viral DNA, and viral RNA.

Embodiment 20

The method according to any one of Embodiments 1 to 19, wherein the protein-nucleic acid complex is formed by a hydrogen bond between the protein and the nucleic acid.

Embodiment 21

The method according to any one of Embodiments 1 to 19, wherein the protein-nucleic acid complex is formed only by a hydrogen bond between the protein and the nucleic acid.

Embodiment 22

The method according to Embodiment 1 to 21, wherein the protein-nucleic acid complex has no covalent bond between the protein and the nucleic acid.

Embodiment 23

The method according to Embodiments 1 to 22, wherein at step (d), a step of treating the protein-nucleic acid complex with a protease is not included.

Embodiment 24

The method according to Embodiments 1 to 22, wherein a step of treating the protein-nucleic acid complex with a protease is not included.

Embodiment 25

The method according to Embodiments 1 to 22, wherein a sonication step is not included for 0.0 minutes or more, 1.0 minutes or more, 2.0 minutes or more, 5.0 minutes or more, 10 minutes or more, or 20 minutes or more.

Embodiment 26

The method according to Embodiments 1 to 22, wherein formaldehyde is not used in an amount of 0% or more, 0.01% or more, 0.02% or more, 0.05% or more, 0.1% or more, 0.2% or more, 0.5% or more, 1.0% or more, 2.0% or more, or 5.0% or more.

Embodiment 27

The method according to Embodiments 1 to 22, wherein ribonuclease (RNase) is not used in an amount of 0 units or more, 0.01 units or more, 0.02 units or more, 0.05 units or more, 0.1 units or more, 0.2 units or more, 0.5 units or more, 1.0 unit or more, 2.0 units or more, or 5.0 units or more.

Advantageous Effects of Invention

According to the present invention, the elimination of use of chaotropic salt and alcohol results in a reduction in time and simplification of a nucleic acid recovery operation and enables provision of a method of concentrating and recovering a protein-nucleic acid complex or a nucleic acid in a sample. A method of concentrating and recovering a protein-nucleic acid complex or a nucleic acid in a sample is an aspect of the present invention, and a method of capturing a protein-nucleic acid complex or a nucleic acid in a sample is another aspect of the present invention.

BRIEF DESCRIPTION OF DRAWINGS

FIG. 1 shows respective amounts of RNA recovered from influenza A viruses by using antibody-bound magnetic particles and antibody-unbound magnetic particles.

FIG. 2 shows respective amounts of RNA recovered from influenza B viruses by using antibody-bound magnetic particles and antibody-unbound magnetic particles.

FIG. 3 shows recovery rates of RNA from influenza A viruses treated with various surfactants when RNA is concentrated by using antibody-bound magnetic particles.

FIG. 4 shows results of detection of EGFR gene T790M mutation in DNAs respectively recovered by using anti-histone antibody-bound magnetic particles and anti-histone antibody-unbound magnetic particles from a serum-free medium in which the human lung cancer cell line NCI-H1975 is cultured.

DESCRIPTION OF EMBODIMENTS

Embodiments of the present invention will now be described in detail.

As used herein, "nucleic acid" is a general term for ribonucleic acid (hereinafter also referred to as RNA) and deoxyribonucleic acid (hereinafter also referred to as DNA) and means nucleotides composed of bases, sugars, and phosphoric acids and linked by phosphodiester bonds. In the present invention, the nucleic acid to be concentrated and recovered may be either DNA or RNA, and the nucleic acid to be targeted may be fragmented or not fragmented. The nucleic acid may be derived from any organisms including animals, plants, and microorganisms and viruses; however, the present invention is not limited thereto. The nucleic acid may be a nucleic acid in a cell nucleus, or an extranuclear nucleic acid retained by organelle represented by mitochondria, chloroplast, nucleolus, etc. Furthermore, the nucleic acid may be an artificially synthesized nucleic acid, or a plasmid or a virus vector generally used as a vector.

As used herein, "protein" means a polymer compound in which an α-amino acid is linked by an amide bond (also referred to as a peptide bond) and may contain a sugar, a dye, etc. in addition to the amino acid.

As used herein, "protein-nucleic acid complex" means a complex in which a protein and a nucleic acid are bound. The protein-nucleic acid complex is typically exemplified by a nucleoprotein and more specifically exemplified by histone proteins forming chromatin, ribonucleoprotein, telomerase, protamine, etc.

In the present invention, a protein is not particularly limited as long as the protein can bind to a nucleic acid contained in a sample; however, in general, a nucleoprotein is a suitable target. For the nucleoprotein, histone is suitable in the case of eukaryote, and the respective nucleoproteins are suitable in the cases of bacteria and virus. For the nucleoprotein of virus, a nucleocapsid protein is preferable.

The binding mode of the protein and the nucleic acid of the present invention is not particularly limited and may be bonded by ionic bond, hydrophobic bond, covalent bond, etc.; however, the protein and the nucleic acid are preferably bonded by the ionic bond or the hydrophobic bond. This is because it is generally considered that the protein and the nucleic acid can easily be dissociated in the case of the ionic bond or the hydrophobic bond.

The antibody applicable in the present invention may be either a monoclonal antibody or a polyclonal antibody as long as the antibody can capture a protein to which a nucleic acid is bound (protein-nucleic acid complex). Although a commercially available product may be applied as the antibody, the antibody can also be uniquely produced by a known method.

For the production of polyclonal antibodies, for example, mice, rats, hamsters, rabbits, goats, sheep, chickens, etc. are used as animals to be immunized. An antiserum can be obtained from a serum after one or more subcutaneous, intradermal, or intraperitoneal administrations of an antigen to the animals. When protein or peptide is used as an antigen, immunization is preferably achieved by a mixture with a complemental liquid having an immunostimulatory effect.

The monoclonal antibodies can be produced by a known monoclonal antibody production method in accordance with, for example, Hideaki Nagamune and Hiroshi Terada, "Monoclonal Antibodiy", Hirokawa Shoten (1990), and James W. Golding, "Monoclonal Antibody", 3rd edition, Academic Press, 1996.

In the present invention, for example, the antibody is preferably an antibody recognizing a nucleoprotein and is more preferably an anti-histone antibody and an antibody recognizing a nucleocapsid protein of a virus.

The antigen used for antibody production is, for example, ccfDNA (circulating cell free DNA, also referred to as cell free DNA) in blood, serum, or plasma, or a histone protein in the case of animal cells described later, respective nucleoproteins in the case of being derived from pathogenic microorganisms described later, and a nucleocapsid protein in the case of being derived from virus, and while a partial fragment (peptide) thereof is usable, crude proteins such as homogenates are also usable (crude: in a natural state; raw; or not processed).

A carrier for immobilizing a commercially available or produced antibody is not particularly limited as long as the antibody can be bound to the carrier, and examples thereof include resins and magnetic beads to which protein A or protein G having high affinity to immunoglobulin, which has been applied to purification of the antibody, is added. Known membranes conventionally used as insoluble membrane carriers for immunochromatographic test strips are also usable. Examples of the membranes include those made of fibers made of polyethylene, polyethylene terephthalate, nylons, glass, polysaccharides such as cellulose and cellulose derivatives, and ceramics. Specific examples thereof include glass fiber filter paper and cellulose filter paper commercially available from Sartorius, Millipore, Toyo Roshi, Whatman, etc.

For a method of preparing a carrier capable of adsorbing the antibody, the method described in US 2010/0248218 or JP 3899029 patent publication (B2), or any method known to those skilled in the art can be used. More specifically, one of specifically binding partners such as biotin-avidin, biotin-streptavidin, reduced glutathione-glutathione S-transferase, etc. can be conjugated to the antibody while the other is supported by a carrier so as to prepare the carrier capable of adsorbing the antibody. Alternatively, a molecule specifically binding to the antibody, such as protein A, protein L, and protein G can be supported by a carrier so as to prepare the carrier capable of adsorbing the antibody.

In a method that is an embodiment of the present invention, after the antibody is immobilized on a carrier, the sample is brought into contact with the antibody-immobilized carrier to allow the antibody-immobilized carrier to capture a protein-nucleic acid complex. In this case, the capturing is preferably achieved by an immunoreaction. In a method that is another embodiment of the present invention, after an antibody specifically reacting with the protein-nucleic acid complex is allowed to act, a protein-nucleic acid-antibody complex obtained by binding of the protein-nucleic acid complex and the antibody is captured by the carrier. The capturing in this case is preferably achieved by physical adsorption (hydrophobic, electrostatic interaction, etc.). In a preferable method, after the antibody is immobilized on a carrier, the sample is brought into contact with the antibody-immobilized carrier to allow the antibody-immobilized carrier to capture a protein-nucleic acid complex. Antibody-bound magnetic particles can be exemplified as the antibody-immobilized carrier.

A method of releasing a nucleic acid from a protein-nucleic acid complex or an antibody-protein-nucleic acid complex can be implemented according to a method known to those skilled in the art (see Cancer Genet. 2018 Mar. 6. pii:S2210-7762(17)30267-3; Transl Lung Cancer Res. 2016 December; 5(6):665-672; J Mol Diagn. 2017 January; 19(1): 162-168; Anal Bioanal Chem. 2015 September; 407(22): 6873-8; PLoS One. 2014 Mar. 3; 9(3):e87838; Cancer Biomark. 2013; 13(5):385-94; Yonsei Med J. 2012 January; 53(1):132-7; Clin Chim Acta. 2009 Jun. 27; 404(2):100-4; QIAamp Circulating Nucleic Acid Handbook October 2013; QIAamp Viral RNA Mini Handbook December 2014).

In this description, regarding a source of the "sample containing a protein-nucleic acid complex", a biological sample described later, or a sample containing a pathogenic microorganism or virus described later is preferable.

As used herein, the "biological sample" means any samples that may be collected from a living body such as blood, plasma, serum, urine, feces, bile, saliva, nasal discharge, nasal cavity/pharyngeal swab, semen, other body fluids and secretions, as well as various organs such as lung, heart, liver, kidney, brain, skin, etc. and crushed materials of tissues therefore. Furthermore, the biological sample may be derived from any organisms including animals, plants, and microorganisms, preferably animals, more preferably mammals, more preferably humans. The animals include, but not limited to, mammals, birds, reptiles, amphibians etc. Mammals include, but not limited to, humans, monkeys, mice, rats, guinea pigs, rabbits, sheep, goats, horses, cows, pigs, dogs, cats, etc. The biological sample may also contain a pathogenic microorganism or virus described later and/or a protein-nucleic acid complex derived from the pathogenic microorganism or virus.

Examples of a sample for concentrating and recovering a nucleic acid from a biological sample preferably include various cells collected from the organisms described above, for example, tissue cells and blood cells, or cells present in urine, feces, saliva, and other body fluids and secretions, and cultured cell lines derived from the organisms described above. Furthermore, examples of the biological sample also include cells characteristic of various diseases (solid cancer, leukemia, etc.). The various cells collected from the organisms are preferably animal-derived cells (also simply referred to as animal cells), more preferably mammalian cells, further preferably human-derived cells.

As used herein, the "sample containing a pathogenic microorganism or virus" means a sample containing a "pathogenic microorganism or virus" described later, or a sample containing a protein-nucleic acid complex derived from the pathogenic microorganism or virus. Examples thereof include a cultured material of a pathogenic microorganism or virus, an inactivated material of a pathogenic microorganism or virus, etc.

As used herein, a pathogenic microorganism or virus means a microorganism or virus among pathogens, and examples thereof include, but not limited to, protozoa, fungi, bacteria, rickettsias, viruses, etc. causing infection.

The pathogenic microorganism or virus applicable to the present invention is not particularly limited as long as the pathogenic microorganism or virus has a protein-nucleic acid complex in which a nucleic acid is bound to a protein. For example, candidates include: Eumycetes such as *Candida* and *Cryptococcus*; Protozoa such as *Plasmodium*, *E. amoeba*, *Trichomonas vaginalis*, *Pneumocystis carinii* pneumonia, and Echinocox; Spirocheta such as *Pallidum Treponema*; bacteria such as *Neisseria gonorrhoeae*, epidemic meningococcus, *Staphylococcus*, *Streptococcus*, *Diplococcus pneumoniae*, *Shigella*, *Escherichia coli*, *Salmonella enterica*, *Vibrio cholerae*, *Pseudomonas aeruginosa*, *Bordetella pertussis*, *Haemophilus influenzae*, *Mycobacterium tuberculosis*, *Clostridium tetani*, *Mycobacterium leprae*, *Corynebacterium diphtheriae*; mycoplasmas; rickettsias; chlamydia; and viruses such as adenovirus, herpes virus, papilloma virus, hepatitis virus, AIDS virus, measles virus, influenza virus, Japanese encephalitis virus, rabies virus, norovirus, and rotavirus.

In the method of the present invention, if the sample contains at least animal cells and/or pathogenic microorganisms or viruses, the sample is treated with a reagent containing a surfactant described later to obtain a concentrate containing a nucleic acid bound to a protein.

Examples of the applicable surfactant include cationic surfactants, anionic surfactants, amphoteric surfactants, nonionic surfactants, etc. One of the features of the present invention is that the use of the surfactant increases the recovery rate of the nucleic acid. Although the mechanism increasing the nucleic acid recovery rate is not clarified, it is presumed that the nucleic acid recovery rate is increased since a lipid bilayer (also referred to as a lipid bilayer membrane) of animal cells and/or pathogenic microorganisms is dissolved and a nucleic acid bound to a protein (protein-nucleic acid complex) is eluted.

Examples of the cationic surfactants include alkylamine salt, quaternary ammonium salt, etc.; examples of the anionic surfactants include cholic acids, alkyl sulfate ester salts, polyoxyethylene alkyl ether sulfate ester salts, alkylbenzene sulfonates, etc.; examples of the amphoteric surfactants include alkylbetaine, alkylamine oxide, cholamide, etc.; examples of the nonionic surfactants include polyoxyethylene alkylether, polyoxyalkylene derivatives, sorbitan fatty acid ester, polyoxyethylene sorbitan fatty acid ester, polyoxyethylene sorbitol fatty acid ester, glycerin fatty acid ester, polyoxyethylene fatty acid ester, polyoxyethylene hydrogenated castor oil, polyoxyethylene alkylamine, alkyl alkanolamide, alkyl imidazolines, alkyl glucoside, alkyl mannoside, alkyl maltoside, trehalose compounds, acyl-N-methylglucamine, etc.

Examples of the cationic surfactants include QUARTAMIN 86P CONC (Kao Corporation) as a commercial product of quaternary ammonium salt. Examples of the anionic surfactants include sodium cholate (Wako Pure Chemical) as a commercial product of cholic acid. Examples of the amphoteric surfactants include AMPHITOL 20BS as a commercial product of alkylbetaine, AMPHITOL 20N (Kao Corporation) as a commercial product of alkylamine oxide, CHAPS and CHAPSO (Dojindo Laboratories) as commercial products of cholamide. Examples of the nonionic surfactants include EMULGEN 120 and EMULGEN 430 (Kao Corporation) as commercial products of polyoxyethylene alkyl ether, and MEGA 8 and MEGA 9 (Dojindo Laboratories) as commercial products of acyl-N-methylglucamine.

As used herein, the "reagent containing a surfactant" means a composition of a surfactant and a buffer.

For the buffer, buffers containing known salt compounds are preferably used. Specific examples include phosphate buffers (phosphate buffered saline (PBS)) and Tris buffers (such as Tris-HCl buffers, TE buffers consisting of Tris and EDTA, TBA buffers consisting of Tris, boric acid, and EDTA).

Regarding a means of treating a sample containing a protein-nucleic acid complex with a reagent containing a surfactant, the reagent may be added to and mixed with the sample. The concentration of the surfactant to be used may appropriately be determined depending on a type to be used and is, for example, 0.01 to 10 mass %, 0.02 to 5 mass %, 0.05 to 2 mass %, and preferably 0.1 to 1 mass % in the sample. The treatment temperature is preferably 5 to 40° C., particularly 10 to 30° C., and the treatment time is preferably 1 to 30 minutes, more preferably 1 to 20 minutes, or 1 to 10 minutes. The sample is preferably diluted 1 to 100 times, 2 to 50 times, particularly 4 to 20 times. In this case, buffers such as phosphate buffers and Tris buffers having pH of around 6 to 9, pH of 6 to 9, pH of 6.5 to 8.5, and pH of 7 to 8 are suitably used.

The present invention will hereinafter be described in detail with examples; however, the present invention is not limited only to these examples.

An example of production of a monoclonal antibody having an influenza virus-derived nucleoprotein as an antigen will be described below as a reference.

Reference Example

Production of Anti-Influenza Virus (A And B) Monoclonal Antibodies

Twenty micrograms of recombinant protein of nucleoprotein (nucleocapsid protein) of human influenza A virus (A/Panama/2007/99) was mixed with an equal amount of a commercially available Freund's complete adjuvant. By using the mixture thereof, mice were subcutaneously immunized three to six times every four to eight weeks. Spleen cells were extirpated from the immunized mice and subjected to cell fusion with myeloma cells (SP/2) by a usual method using polyethylene glycol. For human influenza B virus (B/Shangdon/7/97), the cell fusion was performed with the same procedure as the human influenza A virus.

Anti-influenza virus A monoclonal antibody-producing fusion cells or anti-influenza virus B monoclonal antibody-producing fusion cells (hereinafter, these may simply be referred to as fusion cells) were selected by using an ELISA method. First, virus strains of various subtypes provided from Influenza Virus Research Center of National Institute of Infectious Diseases (also referred to as NIID) (Toyama 1-23-1, Shinjuku-ku, Tokyo) were inactivated to obtain antigens. Wells highly reactive to the obtained antigens were selected, and fused cells were then selected by a usual method of selection according to limiting dilution. For an anti-influenza virus monoclonal antibody, the selected fusion cells were administered into a pristane-treated mouse abdominal cavity and recovered as ascites fluid. IgG (immunoglobulin G) was purified as a specific antibody from the ascites fluid. The specific antibody was purified by using an anion exchange resin.

EXAMPLES

[Example 1] Concentration and Recovery of Viral RNA Using Antibody

In this example, a culture solution of influenza virus was first treated with a reagent containing a surfactant and then brought into contacted with an insoluble carrier to which a specific antibody was immobilized, so as to concentrate and recover RNA of influenza virus.

<Virus Samples>

The following two types of human influenza virus strains were used.

A/California/07/2009 (H1N1) culture solution ($6\times10^6$ copies/µL)

B/Florida/4/2006 culture solution ($6\times10^5$ copies/µL)

<Treatment of Samples>

To 100 µL of a reagent containing a surfactant (20 mM phosphate buffer, 50 mM sodium chloride, 0.5% EMULGEN 120), 1 µL of the culture supernatant was added, mixed, and then allowed to stand at room temperature for 5 minutes.

<Preparation of Antibody-Bound Carrier>

Magnetic particles were used as the insoluble carrier. After separating 50 µL of magnetic particle suspension of DynaBeads Protein G (particle diameter: 2.8 µm, 30 mg/mL; Life Technologies; DynaBeads (registered trademark) Protein G Immunoprecipitation Kit, product number 10007D) and collecting the particles with a magnet, a supernatant was removed. Subsequently, 200 µL of PBST (PBS containing 0.02% Tween 20) containing 30 µg of the anti-influenza A virus monoclonal antibody produced in the reference example was added and stirred at room temperature for 30 minutes to bind (also referred to as immobilize) the antibody to the particles so as to produce antibody-bound magnetic particles. The antibody-bound magnetic particles were washed with PBST and then used for an antigen-antibody reaction. Additionally, 200 µL of PBST (PBS containing 0.02% Tween 20) containing 30 µg of the anti-influenza B virus monoclonal antibody produced in the reference example was added and stirred at room temperature for 30 minutes to bind (also referred to as immobilize) the antibody to particles so as to produce antibody-bound magnetic particles. The antibody-bound magnetic particles were washed with PBST and then used for an antigen-antibody reaction.

<Capture of Viral RNA>

To conduct the antigen-antibody reaction, 100 µL of the treated sample solution above was mixed with the antibody-bound magnetic particles and was subjected to inversion mixing at room temperature for 10 minutes. To confirm whether it is specific capture by the antibody or not, in other words, whether it is nonspecific binding or not, the same operation was performed by using magnetic particles to which no antibody was bound (antibody-unbound magnetic particles).

<Recovery of RNA>

After the magnetic particles were collected with a magnet and the supernatant was removed, RNA adsorbed to the magnetic particles was purified in accordance with a procedure of a commercially available viral RNA purification kit (QIAamp Viral RNA Mini Kit: QIAGEN), and finally, RNA was eluted with 60 µl of nuclease-free water. In this way, an RNA specimen was obtained.

<Confirmation of RNA Recovery>

The amount of RNA captured by the antibody-bound magnetic particles was confirmed by real-time RT-PCR with the following reagents and conditions by using purified RNA as a template.

TABLE 1

| Contents | Volume |
| --- | --- |
| 5 × Buffer (for Q5) | 5 µL |
| 10 mM dNTP | 0.5 µL |
| 10 µM forward primer (SEQ ID NO: 7) | 1.25 µL |
| 10 µM respective reverse primer (SEQ ID NO: 8) | 1.25 µL |
| 20 × EvaGreen | 1.25 µL |
| 2000 U/mL Q5 DNA polymerase | 0.25 µL |
| Nuclease-free Water | 10.5 µL |
| DNA specimen | 5 µL |
| Total | 20 µL |

<Amplification of RNA Derived from Human Influenza Virus A/California/07/2009 (H1N1)>

After reverse transcription at 45° C. for 5 minutes, the reverse transcriptase was inactivated by heating at 95° C. for 30 seconds, and subsequently, a PCR reaction composed of heat denaturation at 95° C. for 3 seconds, annealing and a DNA elongation reaction at 50° C. for 5 seconds, was repeated for 45 cycles.

<Amplification of RNA Derived from Human Influenza Virus B/Florida/4/2006>

The same process was performed as in Amplification of RNA Derived from Human Influenza Virus A/California/07/2009 (H1N1).

[Primers and Probes]

Sequences of primers and probes are described below. Regarding TaqMan Probes of SEQ ID NOS: 3 and 6, the TaqMan Probes were obtained by commissioning Thermo Fisher Scientific to synthesize TaqMan MGB probes. "Q" in SEQ ID NO: 3 and SEQ ID NO: 6 means a "quencher". More specifically, the quencher has an MGB (Minor Groove Binder) structure that is a Tm Enhancer, and a Non Fluorescent Quencher. Although the sequence information of the quencher is not disclosed since this is confidential information of Thermo Fisher Scientific; however, it is a common practice for those skilled in the art to obtain the TaqMan MGB probes by commissioning a synthesizer to synthesize probes. The primers of other SEQ ID Nos were obtained by commissioning Eurofins Genomics to synthesize the primers.

```
For human influenza virus A/California/07/2009
(H1N1)
Forward Primer
                                        SEQ ID NO: 1
5'-CAGTACCAATGAACTGGCGACA-3'

Reverse Primer
                                        SEQ ID NO: 2
5'-AGCTGGAATCAACAAGGATTTACC-3'

TaqMan Probe
                                        SEQ ID NO: 3
5'-FAM-TGAATAGATCGCCAAAAT-Q-3'

For human influenza virus B/Florida/4/2006
Forward Primer
                                        SEQ ID NO: 4
5'-AACACAAATTGAGGTGGGTC-3'
```

-continued

Reverse Primer
SEQ ID NO: 5
5'-CTTTCATAGCACTCYAGAATTCCTGC-3'

TaqMan Probe
SEQ ID NO: 6
5'-FAM-CAACCAATGCCACCATAAA-Q-3'

The results of influenza A virus are shown in FIG. 1, and the results of influenza B virus are shown in FIG. 2. The respective recovered amounts of RNA in the case of using the magnetic particles with the bound antibody (antibody-bound magnetic particles) were $2.8 \times 10^6$ copies (recovery rate 47%) and $2.86 \times 10^5$ copies (recovery rate 48%), and RNA was efficiently recovered. On the other hand, the respective recovered amounts of RNA in the case of using the magnetic particles without the bound antibody (antibody-unbound magnetic particles) were $9.0 \times 10^3$ copies (recovery rate 0.15%: Comparative Example 1) and $6.7 \times 10^3$ copies (recovery rate 1.1%: Comparative Example 2), and the respective recovery efficiencies were lower than when the antibody-bound magnetic particles were used.

[Example 2] Screening of Surfactant in Viral RNA Concentration Using Antibody

The same process as in Example 1 was performed except the following sample treatment process.
<Treatment of Samples>
To 100 µl of reagents (PBS-based) containing the following various surfactants, 1 µl of human influenza virus A/California/07/2009 (H1N1) culture supernatant was added, mixed, and then allowed to stand at room temperature for 5 minutes.
[Surfactants]
The viruses were treated by adding, to PBS, 0.5% EMULGEN 120, 0.5% EMULGEN 430 (Kao Corporation), 70 mM MEGA 8, 30 mM MEGA 9 (Dojindo Laboratories) as non-ionic surfactants, 0.5% QUARTAMIN 86P CONC (Kao Corporation) as a cationic surfactant, 0.5% sodium cholate (Wako Pure Chemical) as an anionic surfactant, 0.5% AMPHITOL 20BS, 0.5% AMPHITOL 20N (Kao Corporation), 10 mM CHAPS, 10 mM CHAPSO (Dojindo Laboratories) as amphoteric surfactants.

The calculation results of the recovery rate in the case of treatment with the various surfactants are shown in FIG. 3. The recovery rate in the case of PBS without addition of a surfactant was about 30%. In contrast, when the surfactants were added, the recovery rate was all 50% or more. From the above, it was confirmed that the rate of recovery of RNA by the antibody is increased by adding the surfactants.

[Example 3] Concentration and Recovery of Human DNA Using Antibody

In this example, human DNA was concentrated and recovered by bringing an insoluble carrier having an immobilized specific antibody into contact with a culture solution containing DNA released due to apoptosis occurring in a human-derived cell line.
<Human-Derived Cell Line>
For the human-derived cell line, NCI-H1975 (transferred from ATCC, CRL-5908 (trade name)) derived from a non-small cell lung cancer patient having an EGFR gene T790M mutation was used. For culturing, first, a serum-free medium (RPMI1640) containing 10% FCS (fetal calf serum, also referred to as fetal bovine serum) was used under the conditions of 37° C. and 5% $CO_2$ until cultured cells reached a confluency of about 80% in the bottom of a culture flask, and the cells were detached with trypsin containing EDTA.

In 10 mL of a serum-free medium (RPMI640), $1 \times 10^7$ recovered cells were suspended and allowed to stand for 5 days under the conditions of 37° C. and 5% $CO_2$. Subsequently, the culture supernatant was centrifuged to obtain a culture solution which was subjected to DNA concentration.
<Preparation of Antibody-Bound Carrier>
After aliquoting 30 µL of magnetic particle suspension of DynaBeads Protein G (particle diameter: 2.8 µm, 30 mg/mL; Life Technologies; DynaBeads (registered trademark) Protein G Immunoprecipitation Kit, product number: 10007D) and collecting the particles with a magnet, a supernatant was removed, and 200 µL of PBST (PBS containing 0.02% Tween 20) containing 20 µg of Histone H4 Polyclonal Antibody (16047-1-AP; Proteintech) was added and stirred at room temperature for 30 minutes to bind (immobilize) the antibody to the particles. The antibody-bound magnetic particles were washed with PBST and then used for an antigen-antibody reaction.
<Capture of DNA in Culture Solution>
To conduct the antigen-antibody reaction, 200 µL of the culture solution above was mixed with the antibody-bound magnetic particles and was subjected to inversion mixing at room temperature for 10 minutes. To confirm whether it is specific capture by the antibody or not, in other words, whether it is nonspecific binding or not, the same operation was performed by using magnetic particles to which no antibody was bound (antibody-unbound magnetic particles).
<Recovery of DNA>
After the magnetic particles were collected with a magnet and the supernatant was removed, ccfDNA adsorbed to the magnetic particles was purified in accordance with a procedure of a commercially available nucleic acid purification kit (QIAamp Circulating Nucleic Acid Kit: QIAGEN), and finally, DNA was eluted with 50 µl of nuclease-free water. In this way, a DNA specimen was obtained.
<Detection of EGFR Gene T790M Mutation in Recovered DNA>
For detection of EGFR gene T790M mutation in the DNA captured by the antibody-bound magnetic particles, 25 µL of reaction solution containing the following reagents was prepared and the DNA was analyzed by using CFX96 (Bio-Rad) with two-step allele-specific PCR.

TABLE 2

| Contents | Volume |
| --- | --- |
| 5 × Buffer (for Q5) | 5 µL |
| 10 mM dNTP | 0.5 µL |
| 10 µM forward primer (SEQ ID NO: 7) | 1.25 µL |
| 10 µM respective reverse primer (SEQ ID NO: 8) | 1.25 µL |
| 20 × EvaGreen | 1.25 µL |
| 2000 U/mL Q5 DNA polymerase | 0.25 µL |
| Nuclease-free Water | 10.5 µL |
| DNA specimen | 5 µL |
| Total | 20 µL |

<Amplification of DNA>
After heat denaturation at 98° C. for 30 seconds, a PCR reaction composed of heat denaturation at 98° C. for 10 seconds, annealing and a DNA elongation reaction at 60° C. for 30 seconds, was repeated for 40 cycles.
[Primers and Probes]
The sequences of the primers are described below. The primers of SEQ ID NOS: 7 and 8 were obtained by commissioning Eurofins Genomics to synthesize the primers.

(allele specific primer)
Forward Primer
SEQ ID NO: 7
5'-CCGTGCATCTCATCTTG-3'

Reverse Primer
SEQ ID NO: 8
5'-CTTTGTGTTCCCGGACATAGTC-3'

The results are shown in FIG. 4. The EGFR gene T790M mutation was successfully detected from the DNA concentrated and recovered by using the magnetic particles to which the antibody was bound. Although a reaction of the mutated gene was observed even when DNA was concentrated and recovered by using magnetic particles to which no antibody was bound (referred to as Comparative Example 3), the reaction arises from the DNA nonspecifically adsorbed to the magnetic particles, and in the comparison of fluorescence intensity at 40 cycles of the PCR reaction, the reaction was as weak as about 1/10 of the reaction with the antibodies.

---

The invention claimed is:

1. A method of concentrating a nucleic acid, comprising the following steps (a) to (d):
 (a) adding a surfactant or a reagent containing a surfactant to a sample containing a protein-nucleic acid complex in which a protein and a nucleic acid are bound, wherein one or more of the protein is selected from the group consisting of histone and nucleocapsid protein, thereby producing a mixture;
 (b) bringing the mixture directly from step (a), an antibody specifically recognizing the protein, and a carrier which can adsorb or is adsorbed to the antibody, into contact with each other;
 (c) recovering the carrier from the sample to obtain the concentrated nucleic acid on the carrier, and
 (d) separating the concentrated nucleic acid from the carrier.

2. The method according to claim 1, wherein at step (b), the carrier brought into contact is an antibody-supporting carrier in which the antibody is adsorbed to the supporting carrier.

3. The method according to claim 2, wherein at step (d), the nucleic acid is released from the protein-nucleic acid complex adsorbed to the antibody-supporting carrier.

4. The method according to claim 1, wherein at step (b), the antibody and the protein-nucleic acid complex are bound to each other to form an antibody-protein-nucleic acid complex.

5. The method according to claim 4, wherein at step (d), the nucleic acid is released from the antibody-protein-nucleic acid complex adsorbed to the carrier.

6. The method according to claim 1, wherein one or more of the surfactant is selected from the group consisting of nonionic surfactants, cationic surfactants, anionic surfactants, and amphoteric surfactants.

7. The method according to claim 1, wherein one or more of the sample is selected from the group consisting of a biological sample and a sample containing a pathogenic microorganism or virus.

8. The method according to claim 7, wherein the biological sample comprises an animal cell.

9. The method according to claim 8, wherein one or more of the biological sample is selected from the group consisting of blood, plasma, serum, urine, feces, bile, pancreatic juice, nasal discharge, and nasal cavity/pharyngeal swab.

10. The method according to claim 7, wherein the sample containing a pathogenic microorganism or virus is a culture of a pathogenic microorganism or virus.

11. The method according to claim 7, wherein the virus is an influenza virus.

12. The method according to claim 1, wherein the nucleic acid is a nucleic acid excluding messenger RNA (mRNA).

13. The method according to claim 1, wherein the nucleic acid is selected from the group consisting of algal DNA, algal RNA, archaeal DNA, archaeal RNA, bacterial DNA, bacterial RNA, catalytic DNA, circular DNA, concatenated DNA, cruciform DNA, fungal DNA, fungal RNA, helminth DNA, helminth RNA, intergenic DNA, isochore, microRNA, neoplasm DNA, neoplasm RNA, nuclear RNA, plant DNA, plant RNA, protozoan DNA, protozoan RNA, recombinant DNA, retroelement, ribosomal DNA, ribosomal RNA, satellite DNA, satellite RNA, transfer RNA, untranslated RNA, viral DNA, and viral RNA.

14. The method according to claim 1, wherein the protein-nucleic acid complex is formed by a hydrogen bond between the protein and the nucleic acid.

15. The method according to claim 1, wherein the protein-nucleic acid complex is formed only by a hydrogen bond between the protein and the nucleic acid.

16. The method according to claim 1, wherein the protein-nucleic acid complex has no covalent bond between the protein and the nucleic acid.

17. The method according to claim 1, wherein at step (d), a step of treating the protein-nucleic acid complex with a protease is not included.

18. The method according to claim 1, wherein a step of treating the protein-nucleic acid complex with a protease is not included in the method.

19. The method according to claim 1, wherein a sonication step is not included or a sonication step for 1.0 minute or more, 2.0 minutes or more, 5.0 minutes or more, 10 minutes or more, or 20 minutes or more, is not included in the method.

20. The method according to claim 1, wherein formaldehyde is not used or formaldehyde is not used in an amount (wt %) of 0.01% or more, 0.02% or more, 0.05% or more, 0.1% or more, 0.2% or more, 0.5% or more, 1.0% or more, 2.0% or more, or 5.0% or more.

21. The method according to claim 1, wherein ribonuclease (RNase) is not used or wherein ribonuclease (RNase) is not used in an amount of 0.01 unit or more, 0.02 unit or more, 0.05 unit or more, 0.1 unit or more, 0.2 unit or more, 0.5 unit or more, 1.0 unit or more, 2.0 units or more, or 5.0 units or more.

* * * * *